United States Patent
Roovers et al.

(10) Patent No.: US 9,936,912 B2
(45) Date of Patent: Apr. 10, 2018

(54) DEVICE FOR MEASURING A CYCLING CADENCE

(71) Applicant: KONINKLIJKE PHILIPS N.V., Eindhoven (NL)

(72) Inventors: David Antoine Christian Marie Roovers, Eindhoven (NL); Laurentia Johanna Huijbregts, Eindhoven (NL); Alphonsus Tarcisius Jozef Maria Schipper, Stramproy (NL); Felipe Maia Masculo, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/116,241

(22) PCT Filed: Feb. 17, 2015

(86) PCT No.: PCT/EP2015/053329
§ 371 (c)(1),
(2) Date: Aug. 3, 2016

(87) PCT Pub. No.: WO2015/128226
PCT Pub. Date: Sep. 3, 2015

(65) Prior Publication Data
US 2017/0007166 A1    Jan. 12, 2017

(30) Foreign Application Priority Data
Feb. 26, 2014    (EP) .................................. 14156690

(51) Int. Cl.
*A61B 5/22*    (2006.01)
*G01C 22/00*    (2006.01)
(Continued)

(52) U.S. Cl.
CPC ............. *A61B 5/222* (2013.01); *A61B 5/0205* (2013.01); *A61B 5/681* (2013.01); *G01C 22/002* (2013.01);
(Continued)

(58) Field of Classification Search
CPC .......... A61B 5/222; A61B 5/00; G01C 19/00; G01C 22/00
(Continued)

(56) References Cited

U.S. PATENT DOCUMENTS 5,568,928 A * 10/1996 Munson ................. A63F 13/06
                                                463/36
7,827,000 B2 * 11/2010 Stirling ................ A61B 5/1038
                                                702/141
(Continued)

FOREIGN PATENT DOCUMENTS

EP    1908401 A1    4/2008
EP    1992389 A1    11/2008
WO   2012052070 A1    4/2012

*Primary Examiner* — Jewel V Dowtin
*Assistant Examiner* — Jewel V. Thompson (57) ABSTRACT

The present invention relates to a device (100) for measuring a cycling cadence, a method (500) of operating a device (100) for measuring a cycling cadence, and a cycling cadence computer program. The device (100) comprises a motion sensor (such as, e.g., an accelerometer) for detecting a movement of the device (100) and for generating a motion signal (x, y, z) corresponding to the movement; a cadence determination unit (300) for determining cycling cadence based on the motion signal (x, y, z). The device (100) can be worn on the cyclist's wrist or arm (110). The motion sensor in the device is able to pick up the tiny movements of the arm or wrist that correspond to the cadence. Optionally, an algorithm is applied that can derive the cadence from a noisy signal.

11 Claims, 3 Drawing Sheets

(51) Int. Cl.
*A61B 5/0205* (2006.01)
*A61B 5/00* (2006.01)
*B62J 99/00* (2009.01)
*A61B 5/024* (2006.01)

(52) U.S. Cl.
CPC ....... *A61B 5/02438* (2013.01); *A61B 2503/10* (2013.01); *B62J 2099/0013* (2013.01)

(58) Field of Classification Search
USPC .......... 600/301; 73/504.08, 379.07; 702/160
See application file for complete search history.

(56) References Cited

U.S. PATENT DOCUMENTS

| | | | | |
|---|---|---|---|---|
| 8,712,723 | B1* | 4/2014 | Kahn | G01B 21/02 |
| | | | | 377/24.2 |
| 2004/0186387 | A1* | 9/2004 | Kosuda | A61B 5/02 |
| | | | | 600/502 |
| 2005/0177059 | A1* | 8/2005 | Koivumaa | A61B 5/0488 |
| | | | | 600/546 |
| 2012/0010478 | A1 | 1/2012 | Kinnunen et al. | |
| 2012/0144554 | A1* | 6/2012 | Thellmann | A63B 21/4033 |
| | | | | 2/161.1 |
| 2013/0151193 | A1 | 6/2013 | Kulach et al. | |
| 2014/0200847 | A1* | 7/2014 | Singiresu | G01P 15/00 |
| | | | | 702/141 |
| 2014/0305204 | A1* | 10/2014 | Hong | A61B 5/7455 |
| | | | | 73/504.08 |
| 2016/0143579 | A1* | 5/2016 | Martikka | A61B 5/486 |
| | | | | 600/301 |

\* cited by examiner

DEVICE FOR MEASURING A CYCLING CADENCE

CROSS-REFERENCE TO PRIOR APPLICATIONS

This application is the U.S. National Phase application under 35 U.S.C. § 371 of International Application No. PCT/EP2015/053329, filed on Feb. 17, 2015, which claims the benefit of European Patent Application No. 14156690.1 filed on Feb. 26, 2014. These applications are hereby incorporated by reference herein, for all purposes.

FIELD OF THE INVENTION

The invention relates to a device for measuring a cycling cadence, a method of operating a device for measuring a cycling cadence, and a cycling cadence computer program.

BACKGROUND OF THE INVENTION

Currently, the rate at which a bicyclist is pedaling, i.e., the cycling cadence, is measured by devices that need to be mounted to the bike, like a magnet on the crank with a sensor on the frame that measures the fluctuating magnetic field when the crank passes closely.

WO2012019654A1 discloses a sensor apparatus for determining a crank cadence and a bicycle speed. The sensor apparatus comprises a housing with an accelerometer with first and second perpendicular measurement axes, capable of providing first and second signals dependent on the two measurement axes, a wireless transmitter, and a power source. The housing comprises an attachment means for attaching the housing to a wheel of the bicycle. The sensor apparatus further comprises a first means for determining the cadence from the rate at which consecutive changes of polarity occur in the first signal, or from the rate at which consecutive positive and negative extreme values occur in the first signal, and a second means for determining the speed from the rate at which consecutive maximum and minimum extreme values occur in the second signal.

EP1992389A1 discloses a data logger for a monitoring sports which includes an accelerometer, a gyro sensor to sense angular displacement, a GPS unit to sense position and velocity, a magnetometer to sense direction of movement, a heart rate monitor, and a controller programmed to manipulate the data and provide a display of the heart rate, speed, and other sport parameters. The data can be stored or transmitted to a remote computer for use by the coach. The device is useful in football codes, athletics, swimming, snow sports and cycling.

A disadvantage of a device attached to the bike for measuring cadence is that it only works on one bike. Most sports cyclists have more than one bike and would thus need to buy and attach a cadence measuring device on each bike. In addition, attaching a cadence meter to a bike is cumbersome.

SUMMARY OF THE INVENTION

It is an object of the present invention to provide a device for measuring a cycling cadence, a method of operating a device for measuring a cycling cadence, and a cycling cadence computer program, which overcome the disadvantages of the prior art.

In a first aspect of the invention, there is provided a device for measuring a cycling cadence. The device comprises a motion sensor for detecting a movement of the device and for generating a motion signal corresponding to the movement. The device further comprises a cadence determination unit for determining a motion-based cadence based on the motion signal. The device further comprises an attachment unit for attaching the device to a wrist or arm.

The solution to the above mentioned disadvantages is to measure the cadence at the wrist or arm. A wrist- or arm-worn device provides for improved mobility because it is not attached to the bike. Attaching the device to a wrist or arm may be done with an attachment unit. The attachment unit may comprise, e.g., a bracelet. However, the device may also be comprised in a watch, and thus be attached to the cyclist's wrist or arm my means of the watch strap. As a cyclist applies a time varying force to the bike pedals, this force results in a small time varying acceleration in the driving direction, which can be measured by the device. However, the present invention is not limited to training while driving an outdoor bicycle. Namely, in the case of an indoor cycle, acceleration in the forward direction is absent, but small rotations are predominant. In fact, a device attached to the wrist or arm of a person exercising on an ergometer slightly rotates as the pedals turn. Thus, in an accelerometer which is subject to gravity, these rotations are measurable as small changes in the orientation of the gravity vector. A motion sensor, such as, e.g., an accelerometer, in the device picks up the tiny movements of the arm or wrist that correspond to the cadence. Based on these detected tiny movements, the motion sensor generates a motion signal. The motion signal may, e.g., correspond to a time-dependent measurement of acceleration. In another embodiment, the motion signal may, e.g., correspond to a time-dependent measurement of gyration. As explained in more detail below, the motion signal may be subjected to a cadence determination unit. The cadence determination unit may process the motion signal to calculate a motion cadence, i.e. an approximated value for the cadence, where the approximation is based on the motion signal.

In an embodiment of the invention, the cadence determination unit is adapted for determining the motion-based cadence by using a frequency of the motion signal. One example for a frequency-based technique relates to a short-term Fourier spectrum. Using the frequency domain rather than the time domain to determine the cadence from the motion signal bears the advantage that frequency based methods are more robust against non-periodic motion. Such non-periodic motion may be caused, for example, by cycling on a rough surface, or by incidental movements of the arm or wrist, such as drinking from water bottle or shifting gears. It is known to those skilled in the art that frequency domain methods are well capable of detecting periodic signal components (i.e. cadence) in the presence of non-periodic noise.

In a further embodiment, the cadence determination unit comprises one or more low-pass filter units for low-pass filtering the motion signal prior to determining the motion-based cadence. When the road surface is rough, the motion sensor (such as, e.g., the accelerometer) measures a considerable amount of noise. The noise may mask the periodic signal component related to the cadence. One possibility to address this issue is by applying low-pass filtering of the motion signal. Since the distortions due to a rough road surface are mainly in the high frequencies (such as, e.g., above 2.5 Hz) and can be extremely large, low-pass filtering may sufficiently suppress noise originating from an uneven road surface. Preferably, the motion signal is classified before subjecting it to low-pass filtering. Namely, the high-frequency component of the motion signal may be use to classify the type of activity (such as, e.g., cycling or walking). Consequently, the cadence determination unit may employ a different algorithm to determine the cadence or may even refrain from determining a cadence altogether (such as, e.g., in cases, where determining a cadence is not meaningful, e.g., if the user is riding a motorcycle or an escalator).

In a further embodiment, the device further comprises an optical sensor. Preferably, the optical sensor is configured such that a light source shines light onto and/or into the skin. Then, reflected, refracted, and/or scattered light is measured at a certain distance from the light source with a photodetector, such as, e.g., a photodiode. Examples of such an optical sensor may be, e.g., sensors that are normally used to measure heart rate or $S_pO_2$ (pulse oximeter oxygen saturation) with reflective ppg (photoplethysmography) or laser speckle sensors. The optical sensor may be comprised in the motion sensor to measure the shifting/tilting of the device with respect to the skin. Especially when the wearer of the device moves his/her arms with the cadence and the device is not completely tightly strapped around the arm/wrist, this shifting/tilting will show the cadence. Further, by providing an optical sensor in addition to the motion sensor, and by using the optical sensor for determining another quantity (such as, e.g., a heart rate), a more complete monitoring of the cycling activity is possible.

In a further embodiment, the optical sensor is configured to generate an optical signal. The cadence determination unit is configured for receiving the optical signal. The cadence determination unit is further configured for determining an optical-signal-based cadence based only on the optical signal, and/or for determining a combined optical motion-based cadence based on a combination of the optical signal and the motion signal.

In a further embodiment, the cadence determination unit is configured for receiving the heart rate signal. Preferably, the cadence determination unit is further configured for determining a heart-rate-based cadence based only on the heart-rate signal, and/or the cadence determination unit is configured for determining a combined heart-rate motion-based cadence based on a combination of the heart rate signal and the motion signal.

In a further embodiment, the device comprises a sensor that is configured for measuring a heart rate and for generating a heart rate signal corresponding to the heart rate. Measuring both heart-rate and cycling cadence includes the advantage that heart-rate and cycling cadence can be easily linked to each other. This may be useful for cyclists who would like to compare both data after the activity. In that case, no manual synchronization of two monitoring devices (namely, a cadence monitor and a heart-rate monitor) would be necessary after the activity.

In a further embodiment, the cadence determination unit comprises a cycling cadence algorithm unit for determining the motion cadence based on the motion signal. Preferably, the cycling cadence algorithm unit employs an algorithm for, first, low-pass filtering the signals to remove high-frequency distortions. Next, the cycling cadence algorithm unit calculates the direction of gravity by averaging each of the x, y and z components for a given time interval. Next, the cycling cadence algorithm unit high-pass filters the signals to observe only the acceleration changes while excluding the DC component of gravity. Eventually, the cycling cadence algorithm unit combines the thusly obtained signals into a signal representing the time varying acceleration in the driving direction. This signal may be subject to the calculation of short term power spectral densities of overlapping signal segments (spectrogram). The peaks in the spectrogram may then be analyzed to determine the cadence. By employing such an algorithm, a smart combination of signals and signal processing is achieved in order to still detect a cadence even under rough road circumstances.

In a further embodiment, the motion sensor comprises an accelerometer. An accelerometer is one possible example for a motion sensor in the present invention. Today, small-sized digital accelerometers are available at affordable prices so that an improved integration of the accelerometer in a watch-like device is possible. The cycling cadence algorithm unit is further configured for determining a horizontal acceleration component. Selecting horizontal acceleration components from the accelerometer signals is advantageous as the distortions are most predominant in the vertical direction.

In a further embodiment, the motion sensor comprises a gyroscope for generating a gyroscope signal. Especially for styles of biking where the biker changes the orientation of his/her arm with the cadence, one or more gyroscopes could also be used to derive the cadence. As noted herein above, in the case of an indoor cycle, acceleration in the "driving" direction is absent, but small rotations are predominant. In fact, a device attached to the wrist or arm of a person exercising on an ergometer slightly rotates as the pedals turn. Thus, in an accelerometer which is subject to gravity, these rotations are measurable as small changes in the orientation of the gravity vector. These rotations may be determined by a gyroscope.

In a further embodiment, the motion sensor further comprises an accelerometer for generating an accelerometer signal. Preferably, the motion signal comprises the gyroscope signal and the accelerometer signal. Preferably, the cadence determination unit is further configured for determining the motion-based cadence based only on the gyroscope signal, and/or based only on the accelerometer signal, and/or based on a combination of the gyroscope signal and the accelerometer signal. Combining accelerometer signals with gyroscope signals may improve the overall signal for deriving the cadence. Namely, when driving a racing bike, a bicyclist will slightly lean to the side when applying force to a pedal. Consequently, the device will change its orientation due to the cyclist's leaning to the side, and, in addition, the device will detect an acceleration (such as, e.g., an acceleration in the driving direction) due to the force applied to the pedal. Correlating the sensor information on both movements will lead to an improved signal, which is more robust to measurement errors.

In a further embodiment, the device further comprises an environment measurement unit configured for measuring one or more environmental parameters. In a further embodiment, the device further comprises a physiology measurement unit configured for measuring one or more physiological parameters. Such direct measurement of environmental and/or physiological parameters obviates not only the need for additional monitor devices, but also improves usability because no afterwards synchronization is necessary. Further, having only one device offers a more compact arrangement, which at the same time is able to measure many parameters of interest to the user.

In a further embodiment, the device comprises a receive unit for receiving input from other measuring units, which measure one or more environmental parameters and/or one or more physiological parameters. Those other measuring units might be installed on the bicycle and/or worn by other users. For instance, each member of a sports team of bicyclists may wear a device according to the present invention. The individual devices may then cross-calibrate each other, e.g., by exchanging information on the noise due to the road surface. Also, a device detecting a significant deviation for a given user (such as, e.g., in heart-rate, cadence, etc.) may notify this to the other devices, which may in turn warn their respective wearers of the deviating condition. Thereby, safety may be increased by monitoring individual health conditions.

In a further embodiment, the one or more environmental parameters comprise height and/or temperature and/or light intensity and/or global positioning and/or humidity and/or wind and/or time. Having an overall picture of the environmental conditions may, e.g., help to classify whether the cyclist is having a bad day or whether a poor training result is rather due to unpleasant weather conditions. Further, the user may record the map driven and correlate his/her positions with the achieved cycling cadence or other parameters.

In a further embodiment, the one or more physiological parameters comprise heart rate and/or blood pressure and/or heart-rate variability and/or respiration rate and/or skin conductance and/or skin temperature and/or core temperature and/or $S_pO_2$ (pulse oximeter oxygen saturation). Having an overall picture of the physiological conditions may be used to individually adapt the training to the cyclist physical condition. For instance, a cyclist may record his/her heart rate etc. and correlate his/her physiological parameters with the cycling cadence. It is noted that an $S_pO_2$ sensor is suitable for being integrated in an arm- or wrist-worn device.

In a further embodiment, the device further comprises a road surface monitor unit for determining an unevenness of a road surface based on the motion signal. Bumps in the road, uneven pavement, speed bumps, etc. give noise on the sensor signals, i.e. they make it harder to derive the cadence. But on the other hand, the noisy sensor signals may be used to determine the unevenness of a road. Namely, the noise itself gives information on the bumpiness of the road. A mountain biker might want to know which part of the training he/she really spent in the woods and how much time it took to cycle to and from the woods. If the bicyclist had recorded the speed during the trip, this would also make the interpretation of the speeds more meaningful. On asphalt, the cadence will be prominently present in the raw motion signals, while on uneven pavement, a high-frequency component will distort the raw motion signal. Therefore, an arm- or wrist-worn device could be made such that it determines (and preferably displays) the bumpiness of the road.

In a further embodiment, the device further comprises a display unit for displaying the cycling cadence in real-time on the device. This embodiment includes the further advantage that the user may—if desired—more or less constantly monitor his/her activity. Namely, a device without a display unit would typically need to be read out afterwards, so that the cyclist does not know about training parameters such as, e.g., the cycling cadence, during cycling. Informing the cyclist about these parameters by, e.g., sound may not be satisfactory, because there may be a lot of acoustic noise on the road, e.g., from passing cars, or, during a race, from spectators, which potentially corrupts the correct transmission of data to the cyclist.

In a further embodiment, the device further comprises a transmit unit for transmitting the measured cadence to another device for measuring cycling cadence. Communicating the cadence to another device for measuring cycling cadence may help to coordinate sports teams driving together in training and/or during a race.

In a further embodiment, the device further comprises a storing unit for storing the cycling cadence data. The storing unit may comprise magnetic storage (such as, e.g., magnetic tape and/or a hard disk drive) and/or optical storage (such as, e.g., a magneto-optical drive and/or an optical disk) and/or electrical storage (such as, e.g., a USB flash drive and/or a solid-state drive). Employing a storing unit facilitates the analysis of training data after an activity, e.g., by means of a more elaborate algorithm, which would need too much computing power on the device itself. The cycling cadence data may comprise the cadence as a function of time or on average determined on-the-fly by the device. The cycling cadence data may further comprise individual motion signals and/or heart-rate signals and/or other physiological parameters and/or environmental parameters etc.

In a further embodiment, the device further comprises an input delivery unit for delivering input for calculating activity and/or energy expenditure. The input delivery unit may comprise a wireless or wired interface to communicate, e.g., an update on a cycling cadence algorithm and/or cadence data recorded with another device etc. Accordingly, the device may be prepared in a backwards-compatible manner (by offering the possibility to install data from other devices) and/or kept up-to-date (e.g., by installing recent versions of a cycling cadence algorithm).

In a further embodiment, the device further comprises a noise indicator unit for indicating that the device is not able to derive the cadence if a cadence cannot be derived from the motion signal. The noise indicator unit may indicate that the device is not able to derive the cadence, e.g., by a sound signal and/or by a visual signal on the device's display or via a lighting element (such as, e.g., a LED) on the device. Situations where a cadence cannot be derived from the motion signal comprise e.g. very uneven roads, where noise due to bumps in the road is too strong to produce a meaningful signal for deriving the cycling cadence. Indicating that the device is not able to derive the cadence does not only prevent the cyclist from checking the device every few seconds in the hope of obtaining a result on the cycling cadence. Indicating that the device is not able to derive the cadence may further help avoiding excessive power consumption by the cadence determination unit. Such excessive power consumption may occur if the motion signal is so noisy that even after applying the cadence algorithm a large number of times, the cadence determination unit is still not able to derive a meaningful value for the cycling cadence.

In a second aspect of the invention, there is provided a method of operating a device for measuring a cycling cadence, the method comprising the steps of attaching the device to a wrist or arm; detecting a movement of the device; generating a motion signal corresponding to the movement; and determining a motion-based cadence based on the motion signal.

In a third aspect of the invention, there is provided a cycling cadence computer program, the cycling cadence computer program comprising program code means for causing a device for measuring a cycling cadence in accordance with the first aspect of the present invention to carry out the steps of the method of operating in accordance with the second aspect of the present invention, when the cycling cadence computer program is run on a computer controlling the device for measuring a cycling cadence.

In a fourth aspect of the invention, there is provided a cycling cadence analysis computer program, the cycling cadence analysis computer program comprising program code means for causing a computer to determine a motion-based cadence based on one or more motion signals, wherein the one or more motion signals are indicative of a movement of a motion sensor, wherein the motion sensor is configured to generate the one or more motion signals in response to the movement. The motion sensor is attached at a wrist or arm of a user during the movement.

It shall be understood that the device and method for measuring a cycling cadence of the claims have silimar and/or identical embodiments as defined in the dependent claims.

DETAILED DESCRIPTION OF EMBODIMENTS

The present invention relates to a device for measuring a cycling cadence, a method of operating a device for measuring a cycling cadence, and a cycling cadence computer program. The device comprises a motion sensor (such as, e.g., an accelerometer) for detecting a movement of the device and for generating a motion signal corresponding to the movement; a cadence determination unit for determining cycling cadence based on the motion signal. The device can be worn on the cyclist's arm or wrist. The motion sensor in the device is able to pick up the tiny movements of the arm or wrist that correspond to the cadence. Optionally, an algorithm is applied that can derive the cadence from a noisy signal. These and other aspects of the invention will be apparent from and elucidated with reference to the embodiments described hereinafter.

Figure 1:
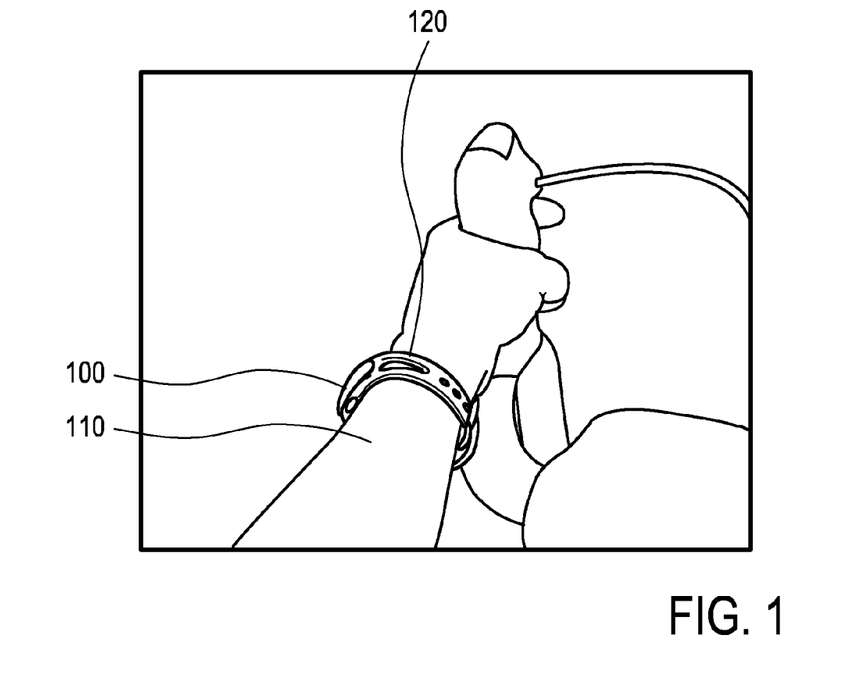
FIG. 1 shows schematically and exemplarily an embodiment of a device for measuring a cycling cadence worn by a user on a sports bike.

FIG. 1 shows an example of a user on a sports bike wearing a watch-like device 100 for measuring cadence. According to the present invention, such a watch-like (or other wrist- or arm-worn device) could be made such that it can derive the cycling cadence. Device 100 comprises an armband or arm straps 120, which are generally suitable for attaching the device 100 to a user's arm or wrist 110.

Figure 2:
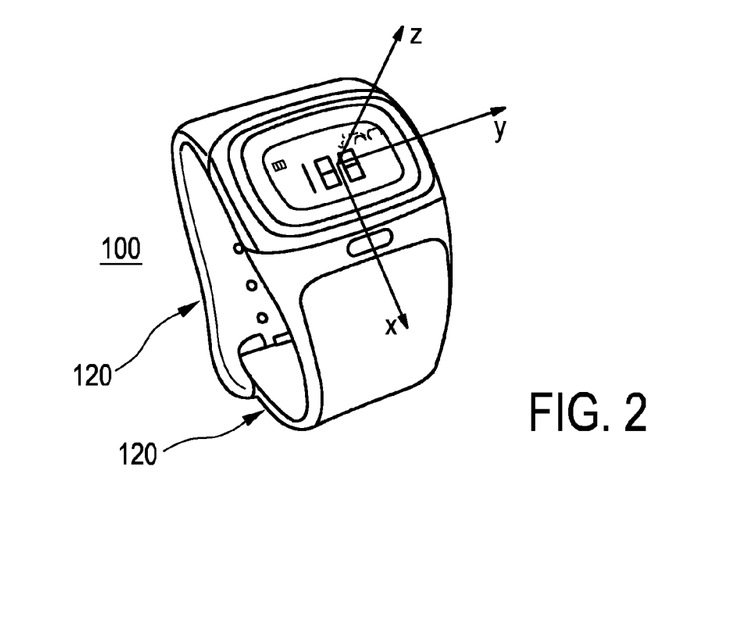
FIG. 2 shows schematically and exemplarily an example of reference axes of an accelerometer integrated in a sports watch.

A 3D-accelerometer could be integrated in a watch-like (or other wrist- or arm-worn) device 100, as illustrated in FIG. 2, showing an example of reference axes of an accelerometer integrated in a sports watch. Motion signals x, y, z for respective axis directions may be communicated to a cadence determination unit (described herein below).

When a person wearing device 100 is cycling while holding the handlebar, the device 100 is subject to several forces such as gravity, translational forces and rotational forces. These are further explained below.

As the person applies a time varying force to the pedals, this force results in a small time varying acceleration, e.g., in the driving direction. The time varying acceleration, and thus the translational force in the driving direction, can be measured by the device 100. Depending on the biking style, the bicycle may also slightly sway from left to right and back as the pedals turn. This translational force from left to right (and back) may result in a small time varying acceleration in the horizontal direction perpendicular to the driving direction.

In the case of an indoor cycle (ergometer), translational forces in the driving direction or from left to right (and back) are virtually absent. In this case, small rotational forces are predominant. It can be observed that a device 100 attached to the wrist or arm 110 of a person (by means of an attachment unit 120) exercising on an ergometer slightly rotates as the pedals turn. While the rotation axis and the detailed shape of these rotations may vary depending on circumstances, rotation of some kind is always observed. In an accelerometer which is subject to gravity, these rotations are measurable as small changes in the orientation of the gravity vector.

Thus, the cadence or pedaling frequency of the person while cycling is observable in the accelerometer signals as a periodic signal. The periodicity can be measured in some suitable way and used to determine the cadence. Cadence may be expressed, e.g., in rounds per minute (rpm).

Additional problems occur when cycling outdoors. Namely, when the road surface is rough, the accelerometer measures a considerable amount of noise, which may easily mask the periodic signal component related to the cadence. The noise may be due to, e.g., bumps, small rocks or other uneven structures in the road surface. A smart combination of signals and signal processing is therefore needed in order to still detect a cadence under such circumstances. Three techniques are mentioned here. These techniques may be part of one or more embodiment of the cadence measuring device according to the present invention.

A first technique relates to low-pass filtering of the acceleration signals. Since the distortions due to a rough road surface are mainly in the high frequencies and can be extremely large, proper low-pass filtering must be applied. Since cycling cadence will typically not exceed 150 revolutions per minute (corresponding to a pedaling frequency of 2.5 Hz), one possibility is to filter out all frequencies above 2.5 Hz. In addition, care must be taken that the analog front end fulfills the requirements to prevent aliasing. In other words, it is advantageous to select the appropriate sample frequency in order to avoid different signals from becoming indistinguishable. Namely, quite high frequent harmonics of the cadence signal and quite high frequent noise from vibrations are part of the acceleration signal.

A second technique relates to selecting horizontal acceleration components from the accelerometer signals. This is advantageous as the distortions coming from an uneven road surface are most predominant in the vertical direction. For instance, small rocks or holes will lead to small movements of the bicycle in the vertical direction, which are, in general, unrelated to the pedaling frequency. Since the direction of gravity is known from the average acceleration direction over a time interval, horizontal and vertical acceleration can be separated by an appropriate rotation of the coordinate system. Furthermore, it may be assumed that the arm of the cyclist is at least approximately pointing in the driving direction. Hence, by projecting the direction in which the arm is pointing (the y direction in FIG. 2) onto the horizontal plane, one may obtain the horizontal acceleration in the driving direction.

A third technique relates to frequency domain techniques for measuring periodicity, such as the short term Fourier spectrum (spectrogram).

Figure 3:
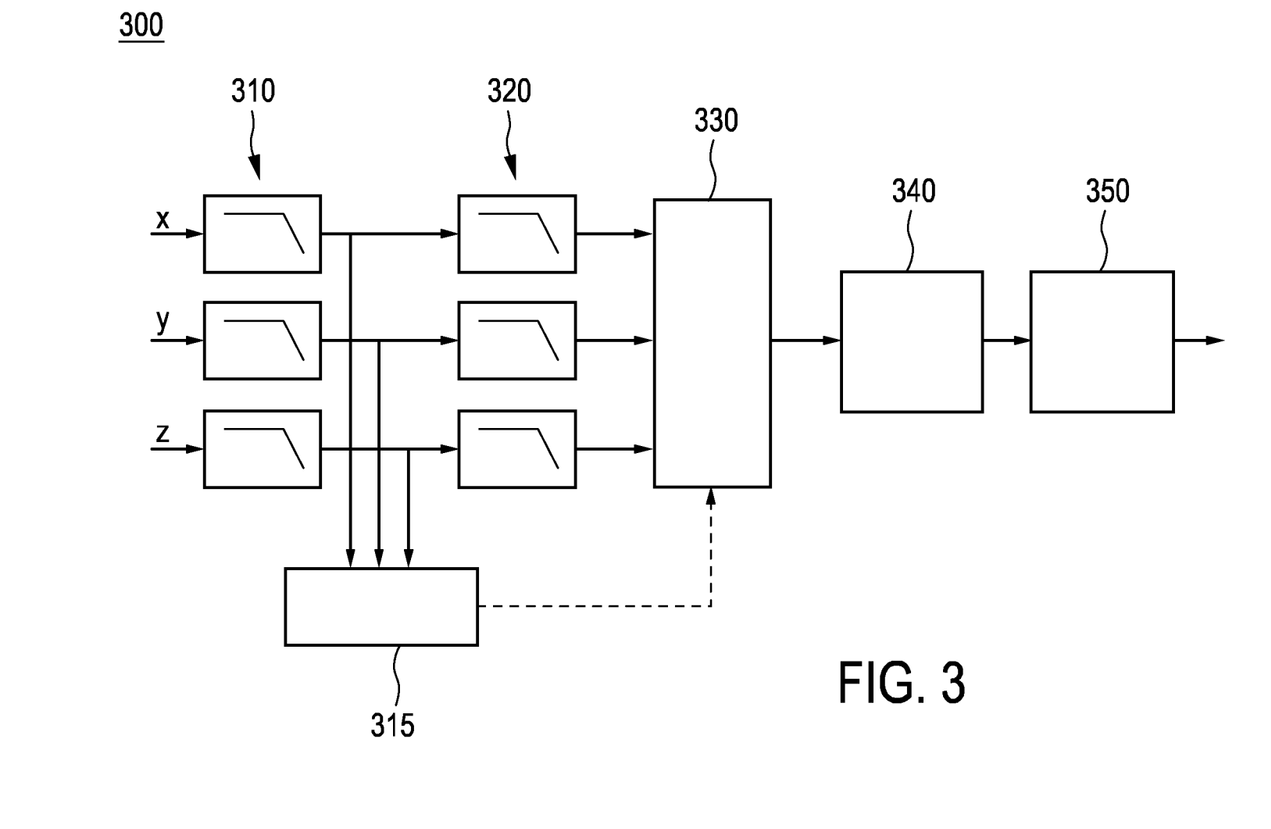
FIG. 3 shows schematically and exemplarily an embodiment of a cadence determination unit.

An embodiment of cadence determination unit 300 is illustrated in FIG. 3. Motion signals x, y, z are low-pass filtered by low-pass filter units 310 to remove high-frequency distortions (e.g., originating from an uneven road surface). The direction of gravity is preferably calculated by optional gravity vector calculation unit 315, which averages each of the x, y and z components for a given time interval. Then, the signals are optionally high-pass filtered by optional high-pass filter units 320 to observe only the acceleration changes while excluding the direct current (DC) component of gravity. This is because the gravitational force does not vary and thus has at most a very low frequency. The embodiment described herein looks for very small periodic signals in a frequency range typically above 30 rpm; removing the relatively large DC component generally improves this detection process. Frequency analysis techniques prefer this large DC term to be removed. Next, optional signal combiner unit 330 may be used to combine the filtered signal components into a single signal representing the time varying acceleration in the driving direction. This signal may be fed to spectrogram calculation unit 340, where it is subject to the calculation of short term power spectral densities of overlapping signal segments (spectrogram). The peaks in the spectrogram are analyzed by cycling cadence algorithm unit 350 to determine the cadence. The last step comprises peak tracking in the spectrogram. It is performed by (1) identifying the peak positions (e.g., by an algorithm searching for local maxima), and by (2) associating the found peak positions with the cadence (see FIG. 4).

Figure 4:
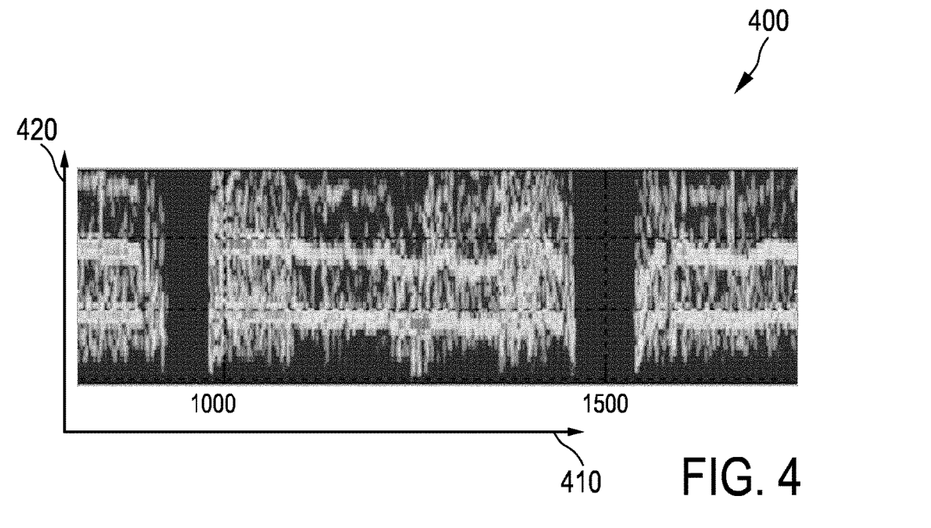
FIG. 4 shows schematically and exemplarily an example of a spectrogram of the band-pass filtered acceleration in the driving direction.

An example of a resulting spectrogram 400 of the band-pass filtered acceleration in the driving direction is shown in FIG. 4. Axis 410 corresponds to a time axis (where, in this example, time is shown in units of seconds). Axis 420 corresponds to the measured band-pass filtered acceleration in the driving direction. For each time slice (along axis 410) the frequency components in the band-pass filtered signal are determined. Thus, axis 420 shows frequency in units of rpm. Both the cadence itself and its second harmonic are clearly visible as traces (i.e., emphasized band-like structures) in the spectrogram. A peak selection algorithm analyzes the spectrogram and determines the fundamental frequency, revealing the cadence. Namely, in the present embodiment, the fundamental frequency equals the cadence. The dashed horizontal lines are at 100 and 200 rpm. Accordingly, in this example, the cadence is 100 rpm. Here, at an interval of approximately 50 seconds before 1000 seconds and another interval after 1500 seconds, no traces are seen at all. These intervals may correspond to times, where, e.g., the cyclist does not pedal, or the cyclist is pedaling with the hands off the handlebar (e.g., when fetching a drink bottle or candy bar, while still pedaling).

Especially for styles of biking where the biker changes the orientation of his/her arm with the cadence, one or more gyroscopes could also be used to derive the cadence. In this case, the cadence would be derived from the change of orientation measured by the one or more gyroscopes. Preferably, accelerometer signals are combined with gyroscope signals to get an improved signal for deriving the cadence.

The accelerometer signal may be further improved by combining the accelerometer signal with that of an optical sensor, where a light source shines light onto and/or into the skin and reflected, refracted, and/or scattered light is measured at a certain distance from the light source with a photodetector, e.g. a photodiode. Examples of such optical sensors are sensors that are normally used to measure heart rate or $S_pO_2$ (pulse oximeter oxygen saturation) with reflective photoplethysmography or laser speckle sensors. The optical sensor may, e.g., measure the shifting or tilting of the device with respect to the skin. For instance, when the wearer of the device moves his/her arms with the cadence and the device is not completely tightly strapped around the arm/wrist, this shifting/tilting will show the cadence. A second component measured with such optical sensors is changes in the amount of blood in and possibly just below the skin. Apart from the blood flow induced by the pumping of the heart, the amount of blood in and just below the skin at the arm/wrist also depends on the tension in the muscles and tendons, on the direction of the arm, and on movements of the arm (movements of the arm result in so-called "sloshing" of blood). All of those are likely to change with the same frequency as the cycling cadence. As different wavelengths are absorbed and scattered differently by the skin and by the blood, signals of different wavelengths are preferably combined (instead of using only one wavelength). In addition, different distances between the photodetector and the light source may be chosen. Further to using the optical signal in combination with the accelerometer signal to get the cadence, the optical signal may be used stand alone for deriving the cadence. In yet another embodiment, the optical signal may be used in combination with a gyroscope. Preferably, the optical signal is also used to derive the wearer's heart rate.

In one embodiment, the hardware of a current watch or bracelet comprising accelerometers is used and an algorithm as described above is added to derive the cadence from the accelerometers in the device. Optionally, the algorithm uses the optical signal to improve the artifact reduction from the accelerometer signals. Preferably, the cadence is displayed in real-time on a display. Heart rate, energy expenditure, time, and possibly other physiological or environmental signals could also be displayed on the display (either on alternating views or on the same view). The data may be stored on the device. The data may however also be transmitted to another device.

Signal noise, for example due to a very uneven road, might be so strong that it becomes fairly impossible to derive the cadence. In that case, instead of displaying a number representing the cadence, the display may show that the device is unable to derive the cadence.

Bumps in the road, uneven pavement, speed bumps, etc. give noise on the sensor signals, i.e. they make it harder to derive the cadence. The algorithm explained herein above makes it in most cases still possible to derive the cadence. However, note that the logic explained herein above to suppress noise from an uneven road surface may also be applied vice versa: Namely, the noise itself gives information on the bumpiness of the road. The structure of the road might be of interest under a number of circumstances. For example a mountainbiker might want to know which part of the training he really spent in the woods and how much time it took to cycle to and from the woods. If he had recorded his speed during his trip, this would also make the interpretation of the speeds more meaningful. On asphalt, the cadence will be prominently present in the raw accelerometer signals, while on uneven pavement, a high-frequency component will clearly distort the raw accelerometer signal. Therefore, an arm- or wrist-worn device could be made such that is displays the bumpiness of the road. However, a device that derives/shows the bumpiness of the road does not need to be attached to the arm/wrist, but could also be attached to other body parts or to the bike.

Figure 5:
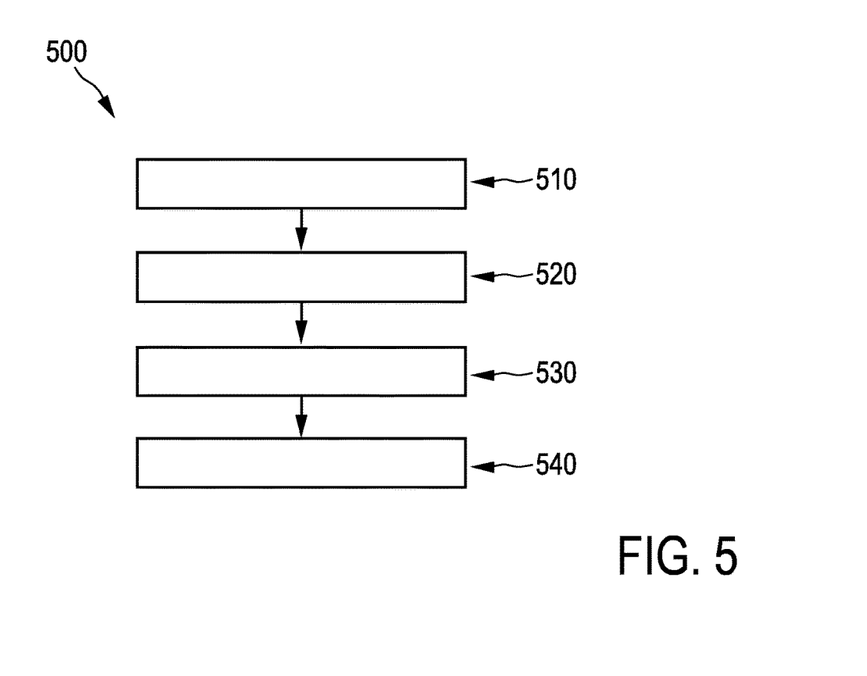
FIG. 5 shows schematically and exemplarily an embodiment of a method of operating a device for measuring a cycling cadence.

FIG. 5 shows schematically and exemplarily an embodiment of a method 500 of operating a device 100 for measuring a cycling cadence. Method 500 starts by attaching device 100 to a wrist or arm 110 (step 510). In a further step 520, method 500 comprises detecting a movement of the device 100. In a further step 530, method 500 comprises generating a motion signal corresponding to the movement. In a still further step 540, method 500 comprises determining a motion-based cadence based on the motion signal.

An example application of the invention resides in determining cycling cadence. A further example application of the invention resides in determining a measure of unevenness of a road surface.

The invention can be used in optical heart-rate watches to which cycling cadence detectors may be added. Besides, there may be interest in tracking the wearer's activities and energy expenditures.

All arrangements of sensors (accelerometers, gyroscopes, optical sensors) can be used with the motion sensor in accordance with the invention.

The motion sensor can comprise one or more accelerometers and/or one or more gyroscopes and/or one or more optical sensors and/or any combination of these sensors.

Although in the above described embodiments certain configurations of the device for measuring a cycling cadence comprising accelerometers are shown, the invention is not limited to a certain configuration of device. In an embodiment, the device does not comprise accelerometers, but only gyroscopes, and/or only optical sensors.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like detecting a movement of the device, determining a motion-based cadence based on the motion signal, measuring a heart rate, determining a heart-rate-based cadence, determining a combined heart-rate motion-based cadence, determining a horizontal acceleration component, measuring one or more environmental parameters, measuring one or more physiological parameters, determining an unevenness of a road surface, et cetera performed by one or several units or devices can be performed by any other number of units or devices. For example, the determination of cadence can be performed by a single unit of by any other number of different units. The determinations and/or the control of the device for measuring a cycling cadence in accordance with the above described method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A device for measuring a cycling cadence, the device comprising:
   a motion sensor for detecting a movement of the device and for generating a motion signal (x, y, z) corresponding to the movement, wherein the motion sensor comprises a gyroscope for generating a gyroscope signal and a single accelerometer for generating an accelerometer signal, and the motion signal (x, y, z) comprises a combination of the gyroscope signal and the accelerometer signal;
   a cadence determination unit for determining a motion-based cadence based on the motion signal (x, y, z); and
   an attachment unit for attaching the device to a wrist or arm.

2. The device for measuring a cycling cadence according to claim 1, wherein the cadence determination unit is adapted for determining the motion-based cadence by using a frequency of the motion signal (x, y, z).

3. The device for measuring a cycling cadence according to claim 1, wherein the cadence determination unit comprises one or more low-pass filter units for low-pass filtering the motion signal (x, y, z) prior to determining the motion-based cadence.

4. The device for measuring a cycling cadence according to claim 1, wherein the device further comprises an optical sensor.

5. The device for measuring a cycling cadence according to claim 4, wherein the optical sensor is configured to generate an optical signal, wherein the cadence determination unit is configured for receiving the optical signal, and wherein the cadence determination unit is further configured for determining an optical-signal-based cadence based only on the optical signal or wherein the cadence determination unit is configured for determining a combined optical motion-based cadence based on a combination of the optical signal and the motion signal (x, y, z).

6. The device for measuring a cycling cadence according to claim 1, wherein the device comprises a sensor that is configured for measuring a heart rate and for generating a heart rate signal corresponding to the heart rate.

7. The device for measuring a cycling cadence according to claim 1, wherein the cadence determination unit comprises a cycling cadence algorithm unit for determining the motion cadence based on the motion signal (x, y, z).

8. The device for measuring a cycling cadence according to claim 7, wherein the cycling cadence algorithm unit is further configured for determining a horizontal acceleration component.

9. The device for measuring a cycling cadence according to claim 1, wherein the device further comprises an environment measurement unit configured for measuring one or more environmental parameters or wherein the device further comprises a physiology measurement unit configured for measuring one or more physiological parameters.

10. The device for measuring a cycling cadence according to claim 1, wherein the device further comprises a road surface monitor unit for determining an unevenness of a road surface based on the motion signal (x, y, z).

11. A method of operating a device for measuring a cycling cadence, the method comprising the steps of:
    attaching the device to a wrist or arm;
    detecting a movement of the device;
    generating a motion signal (x, y, z) corresponding to the movement, wherein the motion signal (x, y, z) comprises a combination of a gyroscope signal from a gyroscope integral with the device and an accelerometer signal from a single accelerometer integral with the device; and
    determining a motion-based cadence based on the motion signal (x, y, z).

* * * * *